US012599312B2

(12) United States Patent
Abkai et al.

(10) Patent No.: US 12,599,312 B2
(45) Date of Patent: Apr. 14, 2026

(54) METHOD FOR ACQUIRING A DENTAL OBJECT

(71) Applicant: DENTSPLY SIRONA Inc., York, PA (US)

(72) Inventors: Ciamak Abkai, Heddesheim (DE); Tim Braun, Grob-Gerau (DE)

(73) Assignee: Dentsply Sirona Inc., York, PA (US)

( * ) Notice: Subject to any disclaimer, the term of this patent is extended or adjusted under 35 U.S.C. 154(b) by 335 days.

(21) Appl. No.: 17/352,457

(22) Filed: Jun. 21, 2021

(65) Prior Publication Data

US 2021/0307637 A1 Oct. 7, 2021

Related U.S. Application Data

(63) Continuation of application No. 15/837,049, filed on Dec. 11, 2017, now abandoned.

(30) Foreign Application Priority Data

Dec. 12, 2016 (EP) ..................................... 16203387

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/1077* (2013.01); *A61B 5/4542* (2013.01); *G01R 33/20* (2013.01);
(Continued)

(58) Field of Classification Search
None
See application file for complete search history.

(56) References Cited

U.S. PATENT DOCUMENTS

| | | | | |
|---|---|---|---|---|
| 4,831,645 A | * | 5/1989 | Guenther | A61B 5/1077 |
| | | | | 378/205 |
| 2010/0074402 A1 | * | 3/2010 | Bothorel | A61B 6/51 |
| | | | | 378/38 |

(Continued)

FOREIGN PATENT DOCUMENTS

EP 3332705 6/2018

OTHER PUBLICATIONS

"Simultaneous Multislice Excitation by Parallel Transmission", Poser et al, Mag. Res. in Med. vol. 71, pp. 1416-1427, (Year: 2014).*

(Continued)

*Primary Examiner* — Michael J Carey
*Assistant Examiner* — Marjan Saboktakin
(74) *Attorney, Agent, or Firm* — SCHWEGMAN LUNDBERG & WOESSNER, P.A.

(57) ABSTRACT

Disclosed herein is a method for acquiring a dental object of a patient with an object volume, in particular at least a part of a skull, an upper jaw and/or a lower jaw. To do so, a plurality of segment volume ranges are defined in the object volume, where the segment volume ranges overlap at most partially and directions of the segment volume ranges are not parallel to one another. The image data of the segment volume ranges is recorded by an MRI machine within a measuring volume of the MRI machine. A two-dimensional composite image is generated from the image data of the individual segment volume ranges by projecting the image data onto a target plane. The target plane is disposed parallel to a defined midsagittal plane of the skull or corresponds to the midsagittal plane, where a first segment volume range at least partially includes the midsagittal plane of the skull.

12 Claims, 3 Drawing Sheets

(51) Int. Cl.

| | | |
|---|---|---|
| *A61B 5/107* | (2006.01) | |
| *G01R 33/20* | (2006.01) | |
| *G06T 7/00* | (2017.01) | |
| *A61C 7/00* | (2006.01) | |
| *G06T 7/50* | (2017.01) | |

(52) U.S. Cl.
CPC ............ *G06T 7/0012* (2013.01); *A61C 7/002* (2013.01); *G06T 7/50* (2017.01)

(56) References Cited

U.S. PATENT DOCUMENTS

| | | | |
|---|---|---|---|
| 2013/0162645 A1* | 6/2013 | Ulrici ....................... | A61B 6/14 |
| | | | 345/424 |
| 2018/0160931 A1 | 6/2018 | Abkai et al. | |
| 2019/0021683 A1* | 1/2019 | Vlachomitrou ...... | A61B 6/4435 |

OTHER PUBLICATIONS

"European Application Serial No. 16203387.2, Extended European Search Report mailed Apr. 25, 2017", w Machine English Translation, 10 pgs.

"European Application Serial No. 16203387.2, Invitation to remedy deficiencies (R. 58 EPC) mailed Feb. 6, 2017", w Machine English Translation, 8 pgs.

"European Application Serial No. 16203387.2, Response filed Feb. 13, 2017 to Invitation to remedy deficiencies (R. 58 EPC) mailed Feb. 6, 2017", w Machine English Translation, 3 pgs.

"U.S. Appl. No. 15/837,049, Non Final Office Action mailed Dec. 21, 2020", 21 pgs.

Eley, Karen A, "Black Bone MRI: a potential alternative to CT with three-dimensional reconstruction of the craniofacial skeleton in the diagnosis of craniosynostosis", European Radiology, Springer International, Berlin, DE, Bd. 24, Nr. 10, (Jul. 20, 2014), 9 pgs.

* cited by examiner

5

METHOD FOR ACQUIRING A DENTAL OBJECT

TECHNICAL FIELD

Disclosed herein is a method for acquiring a dental object of a patient with an object volume, in particular at least a part of a skull, an upper jaw and/or a lower jaw.

BACKGROUND

A number of methods for the preparation of MRI images of dental objects, in particular at least a part of a skull, are known from the state of the art.

According to one known method, individual MRI sectional images, which include, for example, a midsagittal plane or a part of an upper jaw or a lower jaw, are taken by means of a conventional MRI machine. The individual MRI sectional image then represents a defined sectional plane through the patient's skull.

One disadvantage of this method is that the manual planning of the individual MRI sectional images is very time-consuming. The individual MRI sectional images are not continuous, thus making diagnostic analysis difficult.

In another method, a plurality of parallel MRI sectional images can be recorded, allowing a three-dimensional MRI overall image of the entire skull to be generated from the individual MRI sectional images.

One disadvantage of this method is that the measurement of the individual MRI sectional images requires a large amount of measuring time. Another disadvantage of this method is that the entire skull is measured, along with all the anatomical structures contained therein, and the diagnostic analysis of specific structures in the skull of the patient can be made more difficult.

The task of the present invention is therefore to provide a method for acquiring a dental object, in which the recording time is shortened and the image quality of specific structures to be recorded is improved.

SUMMARY

Disclosed herein is a method for acquiring a dental object of a patient with an object volume, in particular at least a part of a skull, an upper jaw and/or a lower jaw. To implement the method, a plurality of segment volume ranges are defined in the object volume, wherein the segment volume ranges overlap at most partially and directions of the segment volume ranges are not parallel to one another, wherein image data of the segment volume ranges is recorded by means of an MRI machine within a measuring volume of the MRI machine, wherein, computer-assisted, a two-dimensional composite image is generated from the image data of the individual segment volume ranges by projecting the image data onto a target plane, wherein the target plane is disposed parallel to a defined midsagittal plane of the skull or corresponds to the midsagittal plane, wherein a first segment volume range at least partially comprises the midsagittal plane of the skull.

The dental object can be at least a part of a skull, a lower jaw and/or an upper jaw. The object can also contain specific anatomical structures, such as the mandibular joints, the alveolar arch, the chin, anterior skull base and/or the edge of the lower jaw.

The MRI machine (magnetic resonance imaging machine) is a conventional MRI machine for measuring a skull. The MRI machine comprises a measuring volume, wherein the object volume of the object is arranged within the measurement volume in order to measure the object. According to one embodiment, a plurality of segment volume ranges are defined within the object volume.

The segment volume ranges can have any desired shape and can, for example, comprise a cuboid geometry. The segment volume ranges can also comprise a curved shape, in which case a special MRI machine that can record such a curved segment volume range is used. In such an MRI machine, the gradient coils can, for example, be arranged in such a way that the isolines of a gradient field are curved.

The image data of the segment volume ranges is then recorded by means of the MRI machine. In a first alternative, the image data of the segment volume ranges is recorded by recording a single three-dimensional MRI overall image of the entire object and cutting the image data of the individual segment volume ranges out of and carrying it over from the three-dimensional MRI overall image. In a second alternative, the image data of the segment volume range is recorded by recording a plurality of MRI segment acquisitions, i.e. at least two MRI segment acquisitions, which display the respective defined segment volume ranges, by means of the MRI machine. This alternative has the advantage that the duration of the entire measurement is decreased, because only the segment volume ranges are measured individually, one after the other.

The segment volume ranges are defined in such a way that, at most, they overlap only partially. The segment volume ranges therefore do not completely contain one another.

A direction of a cuboid segment volume range can be defined, for example, by the longest side edge. In the case of an arbitrarily shaped segment volume range, the direction can also be defined as the largest inner diameter of this segment volume range.

The first segment volume range at least partially comprises the midsagittal plane of the skull, so that particularly significant anatomical structures, such as the skull base, the chin and/or the front teeth, are displayed therein.

The midsagittal plane is a sagittal plane (i.e. a plane which, in a perpendicular viewing direction, shows a lateral view of the body) which divides the head of the patient into two symmetrical halves.

The two-dimensional composite image is generated, computer-assisted, from the image data of the individual segment volume ranges by projecting the image data onto the target plane, which is disposed parallel to the defined midsagittal plane of the skull or corresponds to the midsagittal plane.

The image data of the individual segment volume ranges can also be weighted with defined weighting factors and projected onto the target plane. The weighting factors can, for example, be a function of the demarcation or contrast of the anatomical structures in the individual segment volume ranges. The weighting factors can be calculated dynamically as a function of the anatomical structures, or they can be statically defined. As a result of the different weighting of the individual segment volume ranges, the anatomical structures of the different segment volume ranges can be displayed distinctly with sufficient contrast to one another when superimposed in the composite image. The weighting factors can, for example, have a value of 0.5.

In this way, therefore, a composite image is produced, that corresponds to or replicates a conventional cephalometric radiograph (remote radiography) and can be used, in particular, for cephalometric analysis. As a result of the parallel projection of the image data onto the target surface, the essential distances between defined anatomical structures, such as the anterior skull base, the chin, the mandibular joints, the lower jaw and/or the upper jaw, are not distorted in the cephalometric composite image and can be measured precisely.

Cephalometric diagnostic analysis is used in particular to define an occlusal plane, occlusal height and/or an occlusal curvature. The determined measured variables can then be used in prosthetics, to design a reconstruction in cases of abrasion or to design full dentures consisting of a plurality of teeth. This is because cephalometric diagnostic analysis provides valuable information regarding the positioning of the individual teeth and the jaws in relation to the skull, and in particular regarding the mandibular joint.

One advantage of the present method is that not the entire skull is measured: instead, set segment volume ranges that contain the relevant anatomical structures, such as the upper jaw, the lower jaw, the anterior skull base, the chin and/or the mandibular joints, are defined. The generated two-dimensional composite image, which corresponds to a conventional cephalometric radiograph, thus contains only the projection of the relevant segment volume ranges, so that the remaining intermediate regions of the skull are hidden. This facilitates diagnostic analysis and the determination of the relevant anatomical structures.

In a conventional MRI machine, spatial encoding of the voxels of the measurement volume is performed by allocating the selected signals to the individual volume elements (voxels), wherein the spatial encoding is generated with linearly location-dependent magnetic fields (gradient fields). This makes use of the fact that, for one specific particle, the Larmor frequency depends on the magnetic flux density (the greater the field component perpendicular to the direction of the angular momentum of the particle, the higher the Larmor frequency).

A first gradient is present during excitation and ensures that only one single slice of the body has the appropriate Larmor frequency, i.e. only the spins of this slice are deflected (slice selection gradient).

A second gradient, transverse to the first, is briefly switched on after excitation and effects a controlled dephasing of the spins in such a way that the precession of the spins has a different phase position in each line of the image (phase encoding gradient).

The third gradient is switched at right angles to the other two during the measurement; it ensures that the spins of each column of the image have a different precession velocity, i.e. transmit a different Larmor frequency (readout gradient, frequency encoding gradient).

Together the three gradients thus bring about an encoding of the signal in three spatial planes. The received signal belongs to a specific slice of the body and contains a combination of frequency and phase encoding, which the computer can convert into a two-dimensional image with a Fourier transformation.

A second segment volume range, which comprises at least a part of the upper jaw and/or the lower jaw, can advantageously be defined, wherein the two-dimensional composite image is generated from the first segment volume range and the second segment volume range by projection onto the target plane.

Therefore, in order to generate the two-dimensional composite image, the first segment volume range, with the midsagittal plane, and the second segment volume range, with at least a part of the upper jaw and/or the lower jaw, is projected onto the target plane. In this way, a left half of the upper jaw and/or the lower jaw, for example, can be contained in the second segment volume range. This then allows a cephalometric diagnostic analysis of the left half of the upper jaw or lower jaw in relation to the relevant anatomical structures in the midsagittal plane of the first segment volume range. This type of diagnostic analysis is not possible with conventional cephalometric images, because the structures of the left and the right jaw areas always overlap. The second segment volume range can also comprise the right half of the upper jaw and/or the lower jaw, so that the cephalometric diagnostic analysis of the right half is made possible.

The second segment volume range can advantageously comprise a left side of the upper jaw and/or the lower jaw, wherein additionally a third segment volume range is defined, which comprises a right side of the upper jaw and/or the lower jaw, wherein the two-dimensional composite image is generated from the first segment volume range, the second segment volume range and the third segment volume range by projection onto the target plane.

In this way, therefore, the image data of the first segment volume range with the midsagittal plane, the image data of the second segment volume range with the left side and the image data of the third segment volume range with the right side are superimposed by projection, and the two-dimensional composite image is generated. Ideally, the left mandibular joint of the left side should be brought into superposition with the right mandibular joint of the right side, so that the axis between the two mandibular joints is disposed perpendicular to the target plane (if there is no bifacial asymmetry).

One particular advantage of the present method compared to a conventional cephalometric radiograph, therefore, is that even asymmetries between the left side of the skull and the right side of the skull can be displayed in relation to the midsagittal plane.

Each segment volume range can advantageously be defined in terms of its position and orientation within the measurement volume of the MRI machine on the basis of a presetting for the respective patient, or on the basis of a preliminary image of the object.

The positioning of the patient relative to the MRI machine can, for example, be performed by means of a positioning device, such as a head holder and/or a bite holder. The first segment volume range with the midsagittal plane is then defined in terms of its position and orientation relative to the MRI machine and relative to the positioning device. Depending on the size of the skull of the patient, the two sides of the upper jaw and/or the lower jaw are disposed further away from or closer to the midsagittal plane. The presetting of the MRI machine can, for example, allow the patient to select different programs, for example a children's program or an adult program. To do this, the second segment volume range with the left side of the jaw and the third segment volume range of the jaw, are set in such a way that the jaws of a head template for a child or an adult fit into it. The presetting can also be performed for the respective patient, if the profile and the configuration of the jaws of the patient are already known. The profile and the configuration of the jaws can also be determined from the preliminary image of the patient, whereby the preliminary image can be a two-dimensional image, for example in a transverse plane, or a three-dimensional image. The preliminary image can be a radiograph or an MRI image.

A depth of the segment volume range can advantageously be between 0.5 mm and 30 mm, such as between 1 mm and 15 mm.

The upper jaw and/or the lower jaw is therefore completely contained within the segment volume range, and is thus displayed in its entirety as a projection in the composite image.

The segment volume range can advantageously be cuboid or have a curved elongated shape.

The geometry of the segment volume range is affected by the configuration of the MRI machine and in particular the gradient coils of the MRI machine.

Three gradient coils, which generate the linear gradient fields along the x, y, z-axes of a patient opening, are used in a conventional MRI machine. Thus, by superposition of the gradient fields, an arbitrarily in the space rotatable planar or non-curved surface can obtain a unique resonance frequency. The region excited by means of conventional ID pulses is the excited planar surface extruded along the three surface axes, and thus represents a cuboid oriented arbitrarily in the space.

The composite image can advantageously correspond to a conventional cephalometric radiograph (remote radiography), wherein the target plane of the composite image corresponds to a plane, which is disposed parallel to a detector surface of an X-ray detector in a cephalometric radiograph.

As a result, the generated composite image allows a cephalometric diagnostic analysis of the patient. Compared to a conventional cephalometric radiograph, however, the generated composite image has the advantage that structures between the segment volume ranges are not projected, and are therefore not displayed in the composite image.

The image data of the segment volume ranges can advantageously be recorded by means of the MRI machine, by recording a single three-dimensional MRI overall image of the dental object with the object volume and carrying over the image data of the individual segment volume ranges from the three-dimensional MRI overall image.

In this embodiment, the MRI overall image, for example of the entire skull of the patient, is recorded, wherein the first segment volume range with the midsagittal plane, the second segment volume range with the left side of the jaw and the third segment volume range with the right side of the jaw are cut out of the MRI overall image and carried over.

The image data of the segment volume ranges can advantageously be recorded by means of the MRI machine, by recording a plurality of MRI segment acquisitions, which display the defined segment volume ranges, by means of the MRI machine.

In this alternative embodiment, the individual segment volume ranges are measured individually, whereby an MRI segment acquisition is generated for each segment volume range. To do this, the MRI machine is set in such a way that only one volume within the respective segment volume range is acquired and displayed in the MRI segment acquisition.

The individual MRI segment acquisitions can advantageously be measured incrementally one after the other by means of the MRI machine.

For each MRI segment acquisition, therefore, the MRI machine is reset in order to measure the respective segment volume range. The individual slices of the MRI segment acquisitions are thus read out one after the other, for example by setting the phase encoding gradient in accordance with the spatial encoding.

Advantageously, at least two MRI segment acquisitions can be measured at the same time by means of a special MRI machine based on a multislice excitation method.

The special MRI machine can therefore record the MRI segment acquisitions simultaneously, wherein such an MRI machine allows the excitation of a plurality of slices in the object volume and is based on a so-called multi-pulse excitation method as described in the following technical article (Benedikt A. Poser. Simultaneous multislice excitation by parallel transmission. Magn Reson Med. 2014 April; 71 (4): 1416-1427).

Multiple segment volume ranges can also be recorded simultaneously or in an interleaved manner, by mixing excitation signals and readout signals.

Each MRI segment acquisition can advantageously consist of one single MRI slice image, or it can consist of a stack of multiple MRI slice images.

The MRI segment acquisition can therefore be formed from a single stack of multiple MRI slice images, so that the MRI segment acquisition is either recorded in one step by means of the MRI machine, or in multiple successive steps.

The MRI slice images of a stack can advantageously be disposed parallel to one another within the respective segment volume range.

The MRI slice images are thus measured successively, slice by slice.

The midsagittal plane of the skull can advantageously be defined by positioning the patient relative to the MRI machine by means of a positioning device, or by taking a preliminary image of the skull of the patient and determining the midsagittal plane and/or the position and orientation of the individual segment volume ranges manually by a user or automatically by means of a computer on the basis of the preliminary image.

The midsagittal plane and/or the position and orientation of the individual segment volume ranges are thus determined by means of the positioning device or by means of the preliminary image, so that the target plane parallel to the midsagittal plane and the arrangement of the first segment volume range comprising the midsagittal plane can be defined as a function of the position of the determined midsagittal plane.

The composite image can advantageously be generated in a computer-assisted manner from the image data of the individual segment volume ranges through projection of the image data onto the target plane, by projecting the image data of the individual segment volume ranges onto the target plane in a common projection direction, wherein the projection direction is arranged perpendicular to the target plane.

The image data of the segment volume ranges is therefore projected perpendicularly to the target plane, and thus perpendicularly to the midsagittal plane along the projection direction. Ideally, the left mandibular joint and the right mandibular joint are displayed superimposed in the composite image. Since the distances between the relevant anatomical structures can be measured precisely, this type of composite image makes a precise cephalometric diagnostic analysis of the patient possible.

Prior to the acquisition of the individual segment volume ranges in the object volume, the position and/or the orientation of the segment volume ranges in relation to the MRI machine can advantageously be defined by a user, whereby a head template with an upper jaw template and/or a lower jaw template is schematically displayed by means of a display device, whereby the segment volume ranges and the arrangement thereof in relation to the head template are graphically displayed.

This graphically shows the user where the segment volume ranges and the defined target plane are in relation to the head template. This makes it easier for the user to assess the generated composite image.

The generated composite image can advantageously be displayed by means of a display device.

The composite image can thus be displayed by means of the display device, such as a monitor, so that the diagnostic analysis of the composite image is made easier for a user.

Advantageously, in addition to the composite image, the image data of at least one segment volume range can be displayed by means of the display device.

The user can thus also use the image data of the segment volume ranges for the diagnostic analysis. This is helpful, because only the left side of the jaws, for example, is shown in the second segment volume range, whereas only the right side of the jaws is shown in the third segment volume range.

The image data of the segment volume ranges can be three-dimensional image data or two-dimensional image data. In each case, therefore, one three-dimensional region of the object volume is recorded, i.e. one voxel of the respective segment volume range. Two-dimensional image data thus consists of only one layer of voxels along one of the axes of the respective segment volume range, while three-dimensional image data consists of multiple voxels along all the axes of the respective segment volume range. In both cases, however, the projection is performed in the same manner, namely by projecting the existing voxels (one layer or multiple layers) of the segment volume range along a projection direction, which can be arranged perpendicular to the target plane, onto the target plane and aggregated. Voxels from different layers of the respective segment volume range can therefore be projected onto the target plane.

BRIEF DESCRIPTION OF THE DRAWINGS

The disclosure is explained with reference to the drawings. The drawings show.

DETAILED DESCRIPTION

Figure 1:
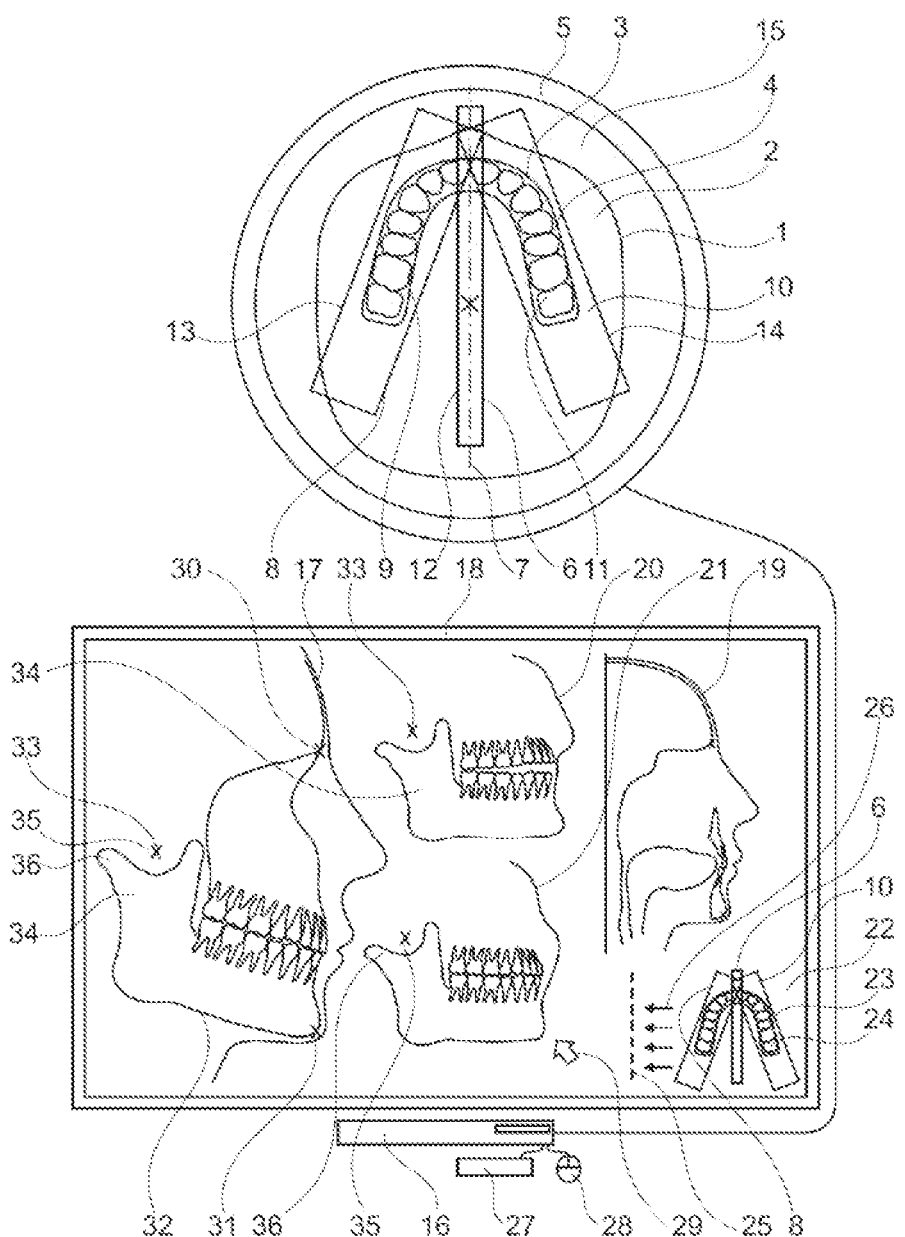
FIG. 1 a sketch to illustrate the present method.

FIG. 1 shows a sketch to illustrate the present method for acquiring a dental object 1, in particular at least a part of a skull 2, an upper jaw 3 and/or a lower jaw 4 by means of an MRI machine 5. A first segment volume range is defined, which at least partially comprises a midsagittal plane 7 that is represented by the dash-dotted line. A second segment volume range 8 comprises a left side 9 of the upper jaw 3 and/or the lower jaw 4. A third segment volume range 10 comprises a right side 11 of the upper jaw 3 and/or the lower jaw 4. The segment volume ranges 6, 8 and 10 are cuboid, and have a direction that is defined by the longest edge of the cuboid segment volume range. A first direction 12 of the first segment volume range 6, a second direction 13 of the second segment volume range 8 and a third direction 14 of the third segment volume range 10 are not parallel to one another. The segment volume ranges 6, 8 and 10 overlap only partially. In a first embodiment, the image data of the segment volume ranges 6, 8 and 10 is cut out of an MRI overall image of the entire head 1. In a second embodiment, the image data of the individual segment volume ranges 6, 8 and 10 is generated by performing individual MRI segment acquisitions of the respective segment volume ranges 6, 8 and 10. The image data recorded within a measuring volume 15 of the MRI machine are transmitted from the MRI machine 5 to a computer 16. By means of the computer 16, a two-dimensional composite image 17 is generated from the image data of the individual segment volume ranges 6, 8 and 10 by projecting the image data onto a target plane, wherein the target plane is disposed parallel to the defined midsagittal plane 7. The midsagittal plane 7 of the skull can be defined by positioning the patient relative to the MRI machine 5 with the aid of a positioning device, such as a head holder or a bite holder, or by analyzing a preliminary image of the patient. The generated composite image 17 can be graphically displayed by means of a display device 18, such as a monitor. In addition to the composite image 17, the first image data 19 of the first segment volume 6, the second image data 20 of the second segment volume 8 and the third image data 21 of the third segment volume 10 can be graphically displayed as well. In a schematic representation 22, a head template with a upper jaw template 23 and/or a lower jaw template 24 can be graphically displayed together with the defined segment volume ranges 6, 8 and 10. The arrangement of the target plane 25 relative to the defined segment volume ranges 6, 8 and 10 and a projection direction 26 can likewise be graphically displayed. The schematic representation 22 facilitates the diagnostic analysis of the composite image 17 and the image data 19, 20 and 21 for the user. Input means, such as a keyboard 27 and a mouse 28, are connected to the computer 16 and enable the operation of a virtual tool via a cursor 29, in order, for example, to manually define the position and orientation of the individual segment volume ranges 6, 8 and 10 or the position of the midsagittal plane 7 or the target plane 25. The composite image 17 corresponds to a conventional cephalometric radiograph for conducting a cephalometric diagnostic analysis. Significant anatomical structures, such as a point 30 of the anterior skull base, a point 31 of the bony chin 32, a left mandibular joint axis 33 of the left mandibular joint 34, a right mandibular joint axis 35 of the right mandibular joint 36, are displayed in the composite image 17. In the present composite image 17, the left mandibular joint axis 33 corresponds to the right mandibular joint axis. The distances between said points 30, 31, 33 and 35 can be determined in the cephalometric diagnostic analysis.

Figure 2:
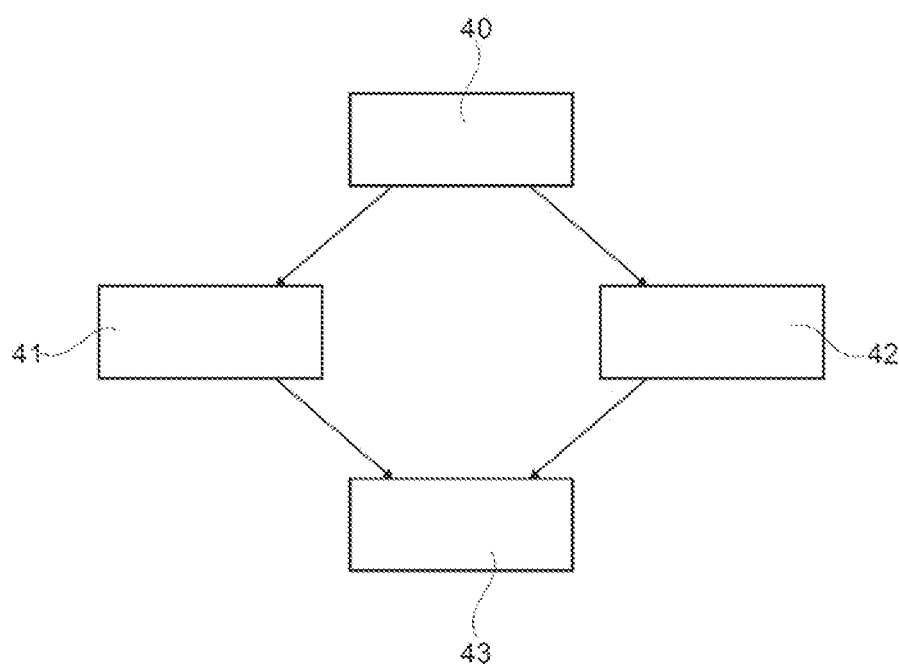
FIG. 2 a schematic flow diagram.

FIG. 2 shows a schematic flow diagram to illustrate an embodiment of the present method. In a first step 40, the segment volume ranges 6, 8 and 10 are defined in relation to the MRI machine. In a first alternative of the second step 41, the image data of the segment volume ranges 6, 8 and 10 is recorded by means of the MRI machine 5, by recording an MRI overall image of the patient's head 1 and cutting the image data of the segment volume ranges 6, 8 and 10 out of the three-dimensional MRI overall image. In a second embodiment of the second step 42, the image data of the segment volume ranges 6, 8 and 10 is recorded by successively measuring individual MRI segment acquisitions by means of the MRI machine 5. In a third step 43, the image data 19, 20 and 21 of the segment ranges 6, 8 and 10 is displayed with the aid of the computer 16 by projection onto the target plane 25, and the composite image 17 is generated.

Figure 3:
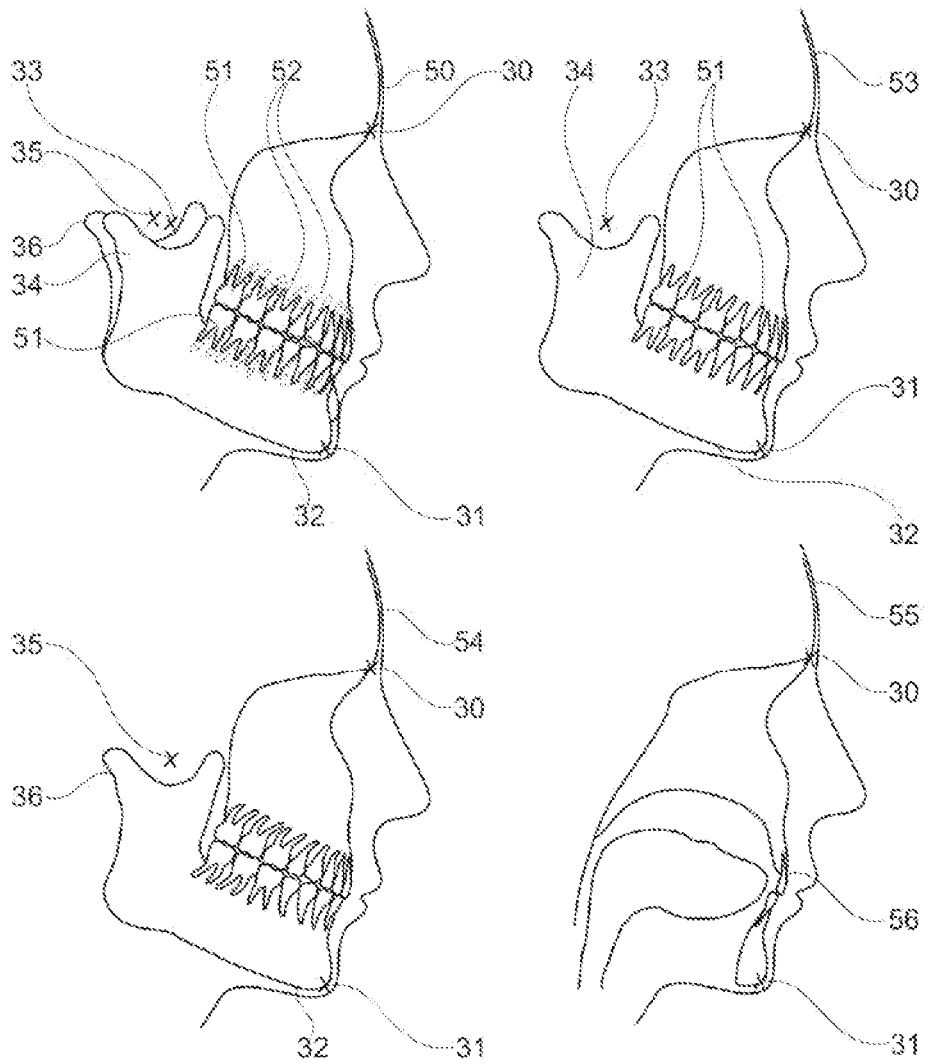
FIG. 3 a sketch with a number of composite images.

FIG. 3 shows a sketch of a variety composite images. As in FIG. 1, the first composite image 50 was generated by projecting the first image data 19 of the first segment volume 6, the second image data 20 of the second segment volume 8 and the third image data 21 of the third segment volume 10 onto the target plane 25.

In contrast to FIG. 1, the patient exhibits bifacial asymmetry, so that the left mandibular joint axis 33 of the left mandibular joint 34 differs from the right mandibular joint axis 35 of the right mandibular joint 36 in the composite image 50. The teeth 51 of the left side of the jaw 9, which are indicated with solid lines, also differ significantly from the teeth 52 of the right side of the jaw 11, which are indicated with dashed lines.

The second composite image 53 was generated by projecting the first image data 19 of the first segment volume 6 and the second image data 20 of the second segment volume 8 of the left side of the jaw 9 onto the target plane 25. As a result, only the left mandibular joint 34 and the teeth 51 of the left side of the jaw 9 are displayed.

The third composite image 54 was generated by projecting the first image data 19 of the first segment volume 6 and the third image data 21 of the third segment volume 10 of the right side of the jaw 11 onto the target plane 25. As a result, only the right mandibular joint 36 and the teeth 52 of the right side of the jaw 11 are displayed.

The fourth composite image 55 was generated by projecting the first image data 19 of the first segment volume 6 onto the target plane 25. As a result, only the anatomical structures 30, 31 and at least partially the incisors 56 from the first segment volume range 6 can be seen along with the midsagittal plane 7.

To enable the user to conduct a better diagnostic analysis, the individual composite images 50, 53, 54 and 55 can be displayed simultaneously next to one another, or also one after the other, by means of the display device 18.

REFERENCE SIGNS

1 Head
2 Skull
3 Upper jaw
4 Lower jaw
5 MRI machine
6 First segment volume range
7 Midsagittal plane
8 Second segment volume range
9 Left side of the jaw
10 Third segment volume range
11 Right side of the jaw
12 First direction
13 Second direction
14 Third direction
15 Measuring volume
16 Computer
17 Composite image
18 Display device
19 First image data
20 Second image data
21 Third image data
22 Schematic representation
23 Upper jaw template
24 Lower jaw template
25 Target plane
26 Projection direction
27 Keyboard
28 Mouse
29 Cursor
30 Point of the anterior skull base
31 Point of the bony chin
32 Chin
33 Left mandibular joint axis
34 Left mandibular joint
35 Mandibular joint axis
36 Right mandibular joint

40 First step
41 Second step
42 Second step
43 Third step
50 First composite image
51 Teeth of the left side of the jaw
52 Teeth of the right side of the jaw
53 Second composite image
54 Third composite image
55 Fourth composite image
56 Incisors

The invention claimed is:

1. A method for acquiring an image of a dental object of a patient, the dental object having an object volume, the method comprising:
    computing a plurality of segment volume ranges in the object volume,
    the plurality of segment volume ranges including a first segment volume range that extends over a left side of a jaw of the patient and is elongated along a first direction that extends generally from a front of the jaw to a rear of the left side of the jaw,
    the plurality of segment volume ranges including a second segment volume range that extends over a right side of the jaw of the patient and is elongated along a second direction that extends generally from the front of the jaw to a rear of the right side of the jaw,
    the first direction and the second direction being on opposite sides of a midsagittal plane of a head of the patient,
    the plurality of segment volume ranges including a third segment volume range that at least partially includes the midsagittal plane of the head of the patient,
    the plurality of segment volume ranges overlapping at most partially proximate the front of the jaw;
    recording, within a measuring volume of a magnetic resonance imaging (MRI) machine, image data of the plurality of segment volume ranges; and
    generating a two-dimensional composite image from the image data of the plurality of segment volume ranges by projecting the image data onto a target plane, wherein the target plane is disposed parallel to the midsagittal plane of the head of the patient.

2. The method of claim 1, wherein with respect to a position and an orientation of each segment volume range within the measuring volume of the MRI machine, said each segment volume range is defined based on a presetting for the patient or based on a preliminary image of the dental object.

3. The method of claim 1, wherein a depth of a segment volume range of the plurality of segment volume ranges is between 0.5 mm and 30 mm.

4. The method of claim 1, wherein the image data of the plurality of segment volume ranges is recorded via the MRI machine, in that a three-dimensional MRI overall image of the dental object with the object volume is recorded, and the image data of the plurality of segment volume ranges is carried over from the three-dimensional MRI overall image.

5. The method of claim 1, wherein the image data of the plurality of segment volume ranges is recorded via the MRI machine, in that a plurality of MRI segment acquisitions, which display the plurality of segment volume ranges, are recorded by the MRI machine.

6. The method of claim 5, wherein the plurality of MRI segment acquisitions are incrementally measured via the MRI machine.

7. The method of claim 5, wherein at least two MRI segment acquisitions are measured simultaneously via the MRI machine that is based on a multislice excitation method.

8. The method of claim 5, wherein each MRI segment acquisition consists of a single MRI slice image or a stack of multiple MRI slice images, wherein a plurality of MRI slice images of a stack are arranged parallel to one another within the plurality of segment volume ranges.

9. The method of claim 1, wherein the two-dimensional composite image and the image data of at least one segment volume range are displayed via a display device.

10. The method of claim 1, wherein:

the first segment volume range is a first cuboid elongated along the first direction;

the second segment volume range is a second cuboid elongated along the second direction;

the third segment volume range is a third cuboid elongated along a third direction; and the first direction, the second direction, and the third direction are not parallel to one another.

11. A method for acquiring a dental image, the method comprising:

capturing, with a magnetic resonance imaging (MRI) machine, three-dimensional MRI data corresponding to a head of a patient;

defining a plurality of segment volume ranges, the plurality of segment volume ranges including a first segment volume range that extends over a left side of a jaw of the patient and is elongated along a first direction that extends generally from a front of the jaw to a rear of the left side of the jaw, the plurality of segment volume ranges including a second segment volume range that extends over a right side of the jaw of the patient and is elongated along a second direction that extends generally from the front of the jaw to a rear of the right side of the jaw, the first direction and the second direction being on opposite sides of a midsagittal plane of the head of the patient, the plurality of segment volume ranges including a third segment volume range that at least partially includes the midsagittal plane of the head of the patient, the plurality of segment volume ranges overlapping at most partially proximate the front of the jaw;

projecting three-dimensional MRI data from the plurality of segment volume ranges onto a target plane that is parallel to the midsagittal plane of the head of the patient;

forming, from the projected three-dimensional MRI data, a two-dimensional composite image of the jaw of the patient; and displaying the two-dimensional composite image on a display device.

12. The method of claim 11, wherein:

the first segment volume range is a first cuboid elongated along the first direction;

the second segment volume range is a second cuboid elongated along the second direction;

the third segment volume range is a third cuboid elongated along a third direction; and the first direction, the second direction, and the third direction are not parallel to one another.

\* \* \* \* \*